United States Patent [19]
Young et al.

[11] Patent Number: 5,352,348
[45] Date of Patent: Oct. 4, 1994

[54] METHOD OF USING ENZYME ELECTRODE

[75] Inventors: Chung Chang Young, Weston; Handani Winarta, Waltham, both of Mass.

[73] Assignee: Nova Biomedical Corporation, Waltham, Mass.

[21] Appl. No.: 970,944

[22] Filed: Nov. 3, 1992

Related U.S. Application Data

[63] Continuation of Ser. No. 628,941, Dec. 14, 1990, abandoned, which is a continuation of Ser. No. 492,316, Mar. 5, 1990, abandoned, which is a continuation of Ser. No. 403,992, Sep. 6, 1989, abandoned, which is a continuation of Ser. No. 152,836, Feb. 5, 1988, abandoned, which is a continuation-in-part of Ser. No. 36,495, Apr. 9, 1987, Pat. No. 4,759,828.

[51] Int. Cl.$^5$ .................. G01N 27/327; G01N 27/404
[52] U.S. Cl. .................. 204/153.12; 204/403; 204/415
[58] Field of Search .................. 204/153.17, 153.12, 204/415, 403

[56] References Cited

U.S. PATENT DOCUMENTS

| | | | |
|---|---|---|---|
| 3,098,813 | 7/1963 | Beebe et al. | 204/415 |
| 3,539,455 | 11/1970 | Clark | 204/415 |
| 3,542,662 | 11/1970 | Hicks et al. | 204/415 |
| 3,575,836 | 4/1971 | Sternberg | 204/415 |
| 3,707,455 | 12/1972 | Derr et al. | 204/415 |
| 3,718,563 | 2/1973 | Krull et al. | 204/415 |
| 3,838,033 | 9/1974 | Mindt et al. | 204/415 |
| 3,869,354 | 3/1975 | Montalvo, Jr. | 204/415 |
| 3,979,274 | 9/1976 | Newman | 204/415 |
| 4,073,713 | 2/1978 | Newman | 204/415 |
| 4,220,503 | 9/1980 | Johnson | 204/415 |
| 4,356,074 | 10/1982 | Johnson | 204/415 |
| 4,388,166 | 6/1983 | Suzuki et al. | 204/403 |
| 4,404,066 | 9/1983 | Johnson | 204/415 |

FOREIGN PATENT DOCUMENTS

| | | | |
|---|---|---|---|
| 0079502 | 5/1983 | European Pat. Off. | G01N 27/30 |
| 0080601 | 6/1983 | European Pat. Off. | G01N 27/30 |
| 0216577 | 1/1987 | European Pat. Off. | |
| 0227029 | 9/1985 | German Democratic Rep. | |
| 0185153 | 9/1985 | Japan | G01N 27/40 |
| 60-185153 | 9/1985 | Japan | |
| 61-145447 | 7/1986 | Japan | |
| 1442303 | 7/1976 | United Kingdom | 204/153.12 |

OTHER PUBLICATIONS

Fischer et al., *Trans. Am. Soc. Artif. Intern. Organs*, 28:245–248, "A Membrane Combination For Implantable Glucose Sensors, Measurements in Undiluted Biological Fluids" (1982).

(List continued on next page.)

*Primary Examiner*—T. Tung
*Attorney, Agent, or Firm*—Fish & Richardson

[57] ABSTRACT

Disclosed is a method of assaying a high concentration of a substance in a liquid sample with a polarographic cell. The cell contains an electrode assembly that includes a reference electrode and a hydrogen peroxide sensor electrode having a laminated membrane covering the liquid sample contacting face of the sensor electrode. The laminated membrane includes an outer membrane permeable to the substance and oxygen, an inner membrane permeable to hydrogen peroxide and located adjacent the face of the sensor electrode, and an enzyme layer between the inner and outer membrane; the enzyme in the enzyme layer can oxidize the substance to generate hydrogen peroxide. The method includes contacting the outer membrane with the liquid sample; permitting the substance and oxygen in the liquid sample to pass through the outer membrane to contact the enzyme layer so that where the substance is oxidized to generate hydrogen peroxide; permitting the generated hydrogen peroxide to pass through the inner membrane to contact the sensor electrode; and ensuring that the supply of oxygen in the enzyme layer relative to the supply of glucose is sufficient to produce an equilibrium concentration of hydrogen peroxide, which generates a steady state response at the sensor electrode proportional to the concentration of the substance in the liquid sample.

8 Claims, 1 Drawing Sheet

OTHER PUBLICATIONS

Feistel et al., Analytical Uses of Immobilized Biological Compounds For Detection, Medical and Industrial Uses, "Design considerations of an immobilized enzyme electrode for measurement of glucose in whole blood", (Series C: Mathematical and Physical Sciences) 226:341–358 (1988).

Wingard Jr., et al., *J. of Biomedical Materials*, "Immobilized enzyme electrodes for the potentiometric measurement of glucose concentration: immobilization techniques and materials", vol. 13 (1979), pp. 921–935.

Iriyama et al., *Jikeikai Medical Journal*, "A convenient method for preparing a glucose sensor", vol. 29, (1982), pp. 889–346.

Clark et al., *Annals of the N.Y. Acad of Sci.*, "Electrode systems for continuous monitoring in cardiovascular surgery", vol. 102, pp. 29–45, (Oct. 31, 1962).

Gough et al., Anal. Chem., "Two-dimensional enzyme electrode sensor for glucose", 57:2351–2357 (Oct. 1985).

METHOD OF USING ENZYME ELECTRODE

This application is a continuation of Ser. No. 07/628,941, filed Dec. 14, 1990, now abandoned; which in turn is a continuation of Ser. No. 07/492,316, filed Mar. 5, 1990, now abandoned; which in turn is a continuation of Ser. No. 07/403,992, filed Sep. 6, 1989, now abandoned; which in turn is a continuation of Ser. No. 07/152,836, filed Feb. 5, 1989, now abandoned; which in turn is a continuation-in-part of Ser. No. 036,495, filed Apr. 9, 1987, now U.S. Pat. No. 4,759,838.

BACKGROUND OF THE INVENTION

The invention relates to enzyme electrodes.

It has previously been proposed To employ enzyme electrodes having laminated membranes for assaying glucose and galactose as described, for example, in Clark U.S. Pat. No. 3,539,455; Newman U.S. Pat. Nos. 3,979,274 and 4,073,713; Johnson U.S. Pat. Nos. 4,220,503, 4,356,074 and 4,404,066; and Japanese Patent Appln. publication 60-185153. Such enzyme electrode assays involve measurement of the enzyme-catalyzed oxidation of glucose or galactose to generate hydrogen peroxide. On electrodes of this type the enzyme is interposed and immobilized between two membranes, the first or outer of which comes into contact with the sample to be assayed and permits access of glucose or galactose and of oxygen to the enzyme from the sample while restricting the passage of proteins, red blood cells, and other macromolecules, and the second of which is in close relationship with the face of the sensor electrode and permits access of hydrogen peroxide to the electrode while at the same time excluding passage of interfering substances having a molecular weight greater than about 250, e.g., ascorbic acid and uric acid. In practice, the sample to be assayed is brought into contact with the outer face of the first or outer membrane. The glucose or galactose in the sample diffuses through the membrane into contact with the immobilized enzyme, leading to the oxidation mentioned above, and diffusion of the resulting hydrogen peroxide through the second or inner membrane into contact with the sensor electrode causes development of an electrical current which can then be read by conventional means, thus enabling determination of the glucose or galactose concentrations by calculations based upon similar measurements made on standard solutions containing known concentrations of the glucose or galactose.

SUMMARY OF THE INVENTION

In general, the invention features, in one aspect, a method of assaying a high concentration (greater than 50 mg/dl) of a substance (e.g., glucose, galactose, lactate, cholesterol) in a liquid sample (e.g., a body fluid such as whole blood, plasma, serum, or urine) with a polarographic cell. The cell contains an electrode assembly that includes a reference electrode and a hydrogen peroxide sensor electrode having a laminated membrane covering the liquid sample contacting face of the sensor electrode. The laminated membrane includes an outer membrane permeable to glucose and oxygen, an inner membrane permeable to hydrogen peroxide and located adjacent the face of the sensor electrode, and an enzyme layer between the inner and outer membrane; the enzyme in the enzyme layer can oxidize the substance to generate hydrogen peroxide. The method includes contacting the outer membrane with the liquid sample; permitting the substance and oxygen in the liquid sample to pass through the outer membrane to contact the enzyme layer so that the substance is oxidized to generate hydrogen peroxide; permitting the generated hydrogen peroxide to pass through the inner membrane to contact the sensor electrode; and ensuring that the supply of oxygen in the enzyme layer relative to the supply of glucose is sufficient to produce an equilibrium concentration of hydrogen peroxide in the enzyme layer and inner layer. The equilibrium concentration of hydrogen peroxide generates a steady state response at the sensor electrode, the response being proportional to the concentration of the substance in the liquid sample.

In preferred embodiments, the supply of oxygen is ensured by using an outer membrane having a thickness (preferably 10–100$\mu$, more preferably 10–20$\mu$) and pore size that hinders the passage of the substance relative to the passage of oxygen.

The hydrogen peroxide generated in the enzyme layer, in addition to passing through the inner membrane, also passes through the outer membrane, contacting the liquid sample. In the preferred embodiments in which the liquid sample is whole blood, the method further includes delaying the passage of hydrogen peroxide through the outer membrane so that the oxidation of hydrogen peroxide by the catalase in the whole blood does not prevent the steady state response. If the passage of hydrogen peroxide is not sufficiently delayed, the oxidation of hydrogen peroxide by the catalase will cause the flow of hydrogen peroxide through the outer membrane to increase, consequently preventing the formation of an equilibrium concentration of hydrogen peroxide in the laminated membrane. The preferred way of delaying the passage of hydrogen peroxide is to use an outer membrane that is thick enough (preferably at least 15$\mu$) to cause the delay; by the time the hydrogen peroxide begins to contact the catalase, an equilibrium concentration of hydrogen peroxide has been generated in the enzyme layer and inner membrane and a steady state response has already been recorded at the sensor electrode.

The invention features, in another aspect, an electrode assembly for performing the featured method. The assembly can obtain a steady state response at high concentrations (e.g., 100 mg/dl) of the substance in liquid samples that contain oxygen concentrations of the range found in undiluted plasma derived from a normal human subject.

The featured method and device provide a means to accurately and consistently measure high concentrations (greater than 50 mg/dl, 100 mg/dl, 200 mg/dl and even as high as 500 mg/dl) of substances that can be oxidized by enzymes to generate hydrogen peroxide. Such substances, e.g., glucose, are commonly found in body fluids, and assays for the substances are useful to the medical community as a diagnostic tool.

Other features and advantages of the invention will be apparent from the following description of the preferred embodiments thereof, and from the claims.

DESCRIPTION OF THE PREFERRED EMBODIMENT

Figure 1:
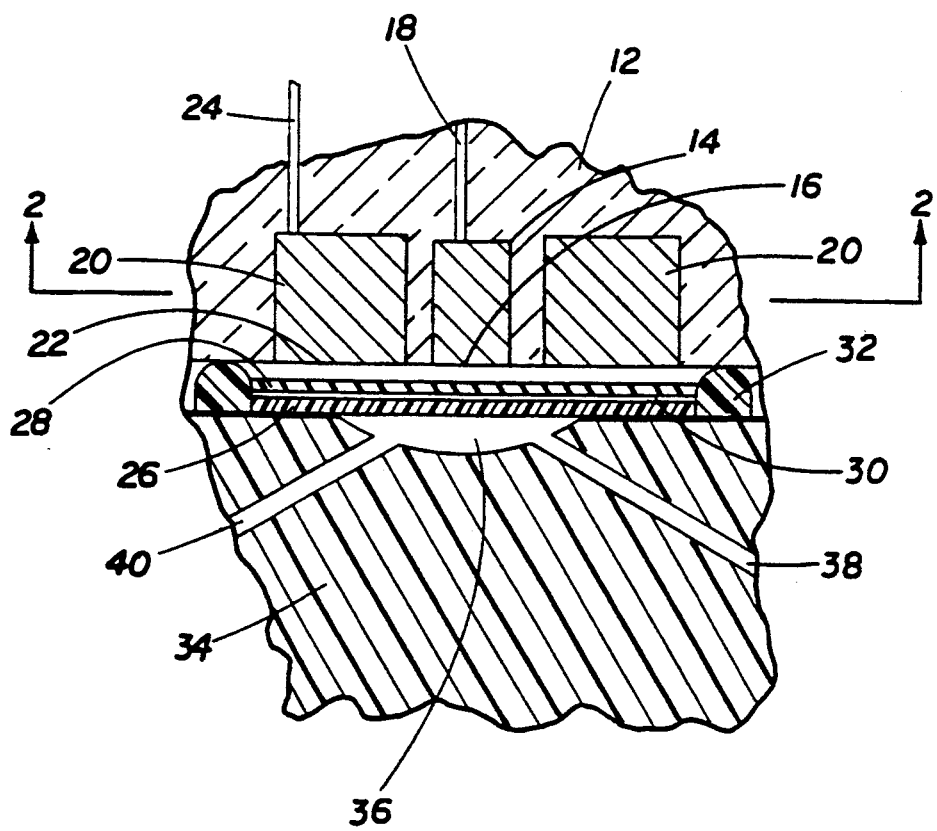
FIG. 1 is a view in section, partially broken away, showing an embodiment of the present invention including a flow chamber, on an enlarged scale.

Referring to the FIG. 1, a glucose electrode 10 comprises an electrically insulating support body 12 which may be of elongated cylindrical shape carrying at its end a platinum sensor electrode or anode 14 having an active or exposed face 16 and a conductor 18. The lower end of the support body 12 also carries a silver/silver chloride reference electrode 20 having an exposed face 22 and a conductor 24. Conductors 18 and 24 lead to an amperometer (not shown). Disposed across the exposed faces of the electrodes is a laminated membrane including an outer membrane 26 and an inner membrane 28 adhesively secured together by an intermediate layer 30 comprising the enzyme glucose oxidase, preferably a mixture of the enzyme and a cross-linking or binding agent such as glutaraldehyde. The laminated membrane is sealed in liquid-tight relation to the lower face of support body 12 by O-ring 32 or any other suitable means.

Outer membrane 26 is preferably polycarbonate but may consist of any other suitable solid porous or permeable material. The pore size and thickness of the membrane 28 are selected to ensure that the passage of glucose into the enzyme layer is sufficiently hindered in comparison to the passage of oxygen that the supply of glucose in the enzyme layer does not exceed the supply of oxygen. In general, the Thicker the membrane and smaller the pore size the more the passage of glucose will be hindered.

The preferred electrode assembly for assaying glucose in fluids not containing catalase has an outer membrane having a thickness of between 8–100$\mu$, more preferably 10–15$\mu$. If the outer membrane is too thin (generally less than about 8–10$\mu$) the glucose molecules may pass through too quickly, and if the outer membrane is too thick (generally greater than 100$\mu$) the glucose molecules will take too long to pass through, causing the electrode assembly to have a poor response time (as high a response time as possible is desirable).

The upper limit on the size of the pore that can be used in membrane 26 and still obtain adequate hindrance of glucose molecules is dependent on the thickness of the membrane. For the more preferred range of thickness (10–15$\mu$) a pore size of about 100 A or less should be used; the lower limit on pore size that should be used is about 10 A, below which an adequate supply of glucose may not pass through.

A pore size of 100 A can also be used effectively in membranes 26 that are greater than 15$\mu$ in thickness, although a larger pore size may also be used. A workable estimate of the upper pore size limit for the thicker membranes can be obtained by using the following formula:

$$t_1/t_2 = (p_1/p_2)^2$$

In the formula $t_1$ is the thickness of a membrane that is known to give adequate results (e.g., 1.2$\mu$); $t_2$ is the known thickness of an alternate membrane; $p_1$ is the known pore size (e.g., 100 A) of the membrane having thickness $t_1$; and $p_2$ is the upper limit pore size that can be used with the membrane having thickness $t_2$.

The above examples of the relationship between pore size and thickness assume that the pore size is the same through the entire thickness of the membrane 26. One skilled in the art will recognize that one layer of the membrane 26 can have one pore size, and a second layer a second pore size. In general, as long as at least a 10–15$\mu$ thick layer of the membrane 26 has a pore size of 100 A or less, it does not matter what the pore size through the remaining layers is. Moreover, one skilled in the art will know how to modify this general approach in accordance with the above formula.

Where the electrode is to be used to assay the concentration of glucose in whole blood, a further factor must be taken into account in selecting an outer membrane 26: whole blood contains catalase, which destroys hydrogen peroxide, and can deter the formation of an equilibrium concentration of hydrogen peroxide in the enzyme layer and inner membrane. In general, to obtain an accurate assay of glucose, the catalase/hydrogen peroxide interaction should be delayed at least until the equilibrium concentration has been generated and a steady state response has been obtained. With electrode 10, this can be accomplished by using an outer membrane having a thickness of at least 15$\mu$; by the time a significant amount of hydrogen peroxide has diffused through an outer membrane of This thickness, an equilibrium concentration of peroxide within the inner membrane and enzyme layer has already been obtained and the response recorded. The most preferred outer membrane for use in whole blood glucose electrodes is about 18$\mu$ thick, a 12$\mu$ thick layer having a pore size of 100 A and 6$\mu$ thick layer having a pore size of 300 A.

The preferred membrane 26 for whole blood should also be used to measure glucose concentrations in other body fluids that contain catalase; for example, if the procedure used to obtain plasma or serum ruptures the red blood cells, catalase will be present.

The outer membrane 26 can be a single membrane, e.g., polycarbonate membrane, of the desired thickness and pore size, or may be a plurality of thinner membranes affixed to each other (e.g., using a Bovine Serum Albumin-glutaraldehyde binder) to yield one membrane of the desired thickness. For example, the most preferred outer membrane 26 for whole blood is made by combining two 6$\mu$ thick membranes having a 100 A pore size and a 6$\mu$ thick membrane having a 300 A pore size.

Inner membrane 28 may be of silicone rubber, methyl methacrylate or other suitable porous and permeable material, e.g., cellulose acetate butyrate, and preferably comprises cellulose-acetate. It has a thickness of 2–10$\mu$, more preferably 2–4$\mu$. If membrane 28 is thicker than 10$\mu$, the passage of hydrogen peroxide through the layer may be too slow. If the membrane is thinner than 2$\mu$, it may not be strong enough. Membrane 28, while permitting the quick passage of hydrogen peroxide, is a barrier to the passage of other low molecular weight substances (e.g., ascorbic acid, uric acid) that may interfere with measurements made by anode 14; substances such as ascorbic acid and uric acid are often present in samples being analyzed and readily pass through outer membrane 26.

Glucose oxidase layer 30 most preferably is a mixture of the enzyme and a cross-linking agent such as glutaraldehyde.

In the embodiment shown in FIG. 1, a flow cell 34 is mounted in liquid-tight relation against the lower face of outer membrane 26, being sealed thereto by a silicone washer or by O-ring 32. Cell 34 may be constructed of polystyrene, polymethacrylate, or any other suitable rigid liquid impervious material and includes a chamber 36 exposed to the face of outer membrane 26 as well as inlet 38 and outlet 40. In a preferred embodiment, the volume of chamber 36 together with inlet 38 and outlet 40 is approximately 5 to 10 microliters.

In general, in preparation of the laminated membrane a cellulose acetate solution in 1:1 acetone:cyclohexanone is spread on the surface of a glass plate using a microfilm applicator (available from the Paul N. Gardner Co., Pompano, Fla., Cat. No. AP-M02). After air drying, a thin film is formed on the glass surface. A mixture of enzyme, buffer solution, and glutaraldehyde is coated on the surface of the film using the applicator; the formulation contains, per ml of distilled water, 50 mg glucose oxidase, 12 mg disodium succinate hexahydrate, 1.5 mg succinic acid, 0.3 mg sodium benzoate, 75 $\mu$g dipotassium EDTA, and 2.5%, by volume, glutaraldehyde. A polycarbonate membrane (of the type available from Nuclepore Corp., Pleasanton, Calif.) is placed on top of the solution, and excess solution is squeezed out using a roller. After drying, in those embodiments using a plurality of polycarbonate membranes, which together make up outer membrane 26, a mixture of Bovine Serum Albumin (BSA) and glutaraldehyde (the mixture containing, per ml of distilled water, 100 mg BSA and 0.25%, by volume, glutaraldehyde) is spread on the surface of the underlying polycarbonate membrane using the microfilm applicator, the second membrane is placed on top, and the excess solution is squeezed out. After air drying, additional polycarbonate membranes can be added in analagous fashion.

Figure 2:
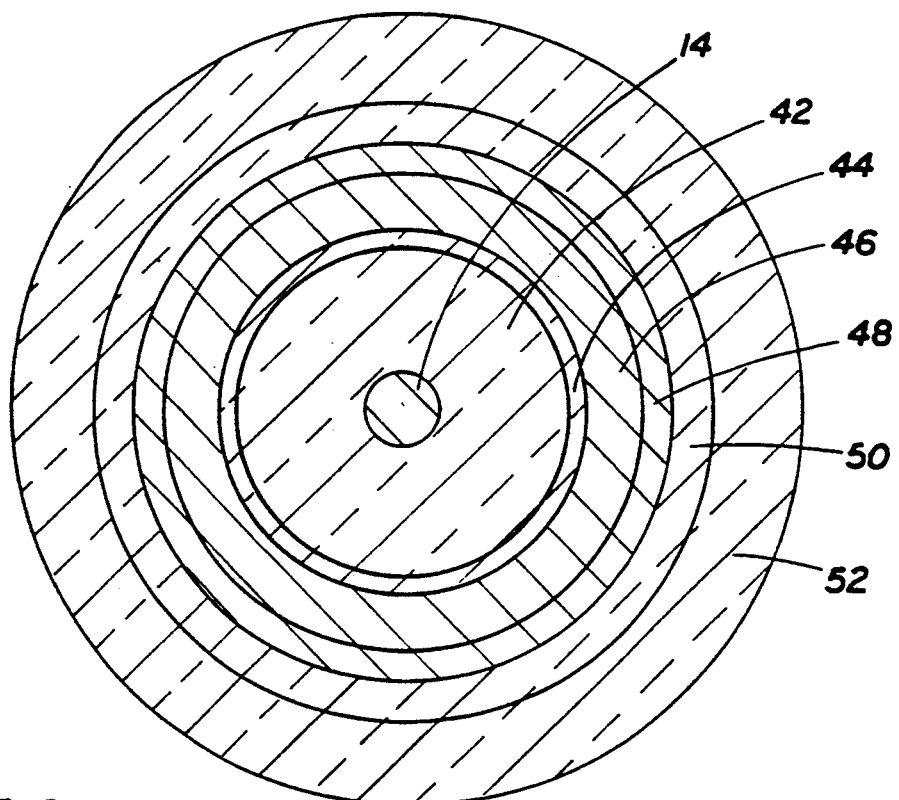
FIG. 2 is a view in section at 2—2 of FIG. 1.

Referring to FIG. 2, the support body 12 has 0.016 inch diameter central platinum sensor electrode 14 surrounded by concentric rings including one of lead glass (42) (0120 type; 0.095 inch O.D.); versilok structural adhesive (44) (0.005 inch thick); silver (46) (0.015 inch I.D.; 0.125 inch O.D.); a 60-40 mixture of silver sulfide (AgS)-silver chloride (AgCl) (48) (0.01 inch thick); potting material epoxy (50) (0.02 inch thick); and Noryl (52) (0.337 inch O.D.). Rings 46 and 48 are the silver/silver chloride reference electrode 20. The AgCl ring 48 provides an adequate supply of silver ion so that the changes in potential at the reference electrode caused by the current is minimal. A reference electrode having an 0.01 inch thick ring can be used for thousands of measurements; a counter electrode is not needed with the assembly. In general, the AgCl ring should be at least 25$\mu$ thick to provide the adequate supply of silver ion; there is no real upper limit on thickness, although as a practical matter the ring probably should not be thicker than about 0.5 cm.

In a typical assay, a body fluid, e.g., whole blood, is flowed through the inlet 38 and fills the sample chamber 36. When the outer membrane 26 contacts the whole blood, glucose molecules and oxygen molecules present in the sample pass through it and contact the enzyme in layer 30; the enzyme catalyzes the oxidation of glucose to gluconic acid. The hydrogen peroxide produced during the oxidation passes through membrane 28 and contacts surface 16 of sensor electrode 14, which is poised at +700 mV in relation to reference electrode 20, and also contacts the face 22 of reference electrode 20, forming an electroconductive path between the two electrodes. A current is generated, the magnitude rising to a constant (steady state) value (response) related to the equilibrium concentration of the hydrogen peroxide. The outer membrane 26 limits the passage of glucose sufficiently so that the supply of oxygen is not the rate limiting factor in the oxidation, thus ensuring that a steady state response is obtained.

The hydrogen peroxide generated in enzyme layer 30 also diffuses through the outer membrane 26 and contacts the whole blood, which contains the catalase that destroys hydrogen peroxide. This consumption causes the diffusion of hydrogen peroxide from the layer 30 through the outer membrane to increase, thus upsetting the equilibrium concentration of hydrogen peroxide in the laminated membrane in general and the rate of mass transfer of hydrogen peroxide to the surface of the two electrodes in particular. Under these circumstances, the current will not be at a steady state value, and accurate measurements of glucose concentration can not be obtained. Outer membrane 26 of the electrode is of sufficient thickness that by the time the hydrogen peroxide passes through the layer and contacts whole blood, an accurate steady state current has already been obtained and recorded.

Other Embodiments

Other embodiments are within the following claims. For example, the electrode can be designed to assay other substances besides glucose, provided the enzyme in the layer 30 oxidizes the substance to generate hydrogen peroxide. Thus, where lactate oxidase was substituted for glucose oxidase in the preferred embodiment, concentrations of lactate in whole blood were assayed. Similarly, concentrations of cholesterol can be assayed where the enzyme is cholesterol oxidase, and concentrations of ethanol can be assayed where the enzyme is alcohol oxidase.

One skilled in the art will recognize that a standard counter electrode can be used in conjunction with the sensor and reference electrodes, if desired.

We claim:

1. A method of assaying the concentration of a substance in an undiluted whole blood or undiluted plasma sample, which includes catalase, comprising providing a polarographic cell that includes an electrode assembly comprising a reference electrode and a hydrogen peroxide sensor electrode having a laminated membrane covering a sample-contacting face of said sensor electrode, said laminated membrane comprising an outer membrane permeable to said substance and oxygen while preventing the passage of proteins and red blood cells, an inner membrane permeable to hydrogen peroxide and located adjacent the face of said sensor electrode, and an enzyme layer between said inner membrane and said outer membrane, said enzyme layer comprising an enzyme that can oxidize said substance to generate hydrogen peroxide, said outer membrane having pores that allow passage of said substance and oxygen from said undiluted sample to said enzyme layer, the thickness of said outer membrane and the size of said pores being selected so that said passage of said substrate is sufficiently hindered relative to said passage of said oxygen that a steady state response proportional to the substance concentration with said electrode assembly can be obtained at substance concentrations in an undiluted whole blood sample of at least 300 mg/dl where the oxygen concentration is equivalent to the oxygen concentration in a plasma sample derived from a normal human subject, and said outer membrane having a thickness of between 20 and 100$\mu$ to impair the passage of hydrogen peroxide from said enzyme layer to said undiluted sample to an extent great enough to permit said steady state to be reached;

contacting said outer membrane with said undiluted sample comprising said substrate to permit said substance and oxygen in said undiluted sample to pass through said outer membrane to said enzyme layer so that said enzyme oxidizes said substance to generate hydrogen peroxide, said generated hydrogen peroxide passing through said inner layer to contact said face of said sensor electrode;

maintaining said contact between said outer membrane and said undiluted sample for a sufficient period of time to generate a steady state responses proportional to the substrate concentration; and measuring said steady state response to determine said substrate concentration.

2. The method of claim 1 wherein said outer membrane has a thickness of between 18 and 100μ.

3. The method of claim 1 wherein said substance is glucose and said enzyme is glucose oxidase.

4. The method of claim 1 wherein said substance is lactate and said enzyme is lactate oxidase.

5. The method of claim 1 wherein said substance is alcohol and said enzyme is alcohol oxidase.

6. The method of claim 1 wherein said substance is cholesterol and said enzyme is cholesterol oxidase.

7. The method of claim 1 wherein said sample is undiluted whole blood.

8. The method of claim 1 wherein said sample is undiluted plasma.

* * * * *

UNITED STATES PATENT AND TRADEMARK OFFICE
CERTIFICATE OF CORRECTION

PATENT NO.   : 5,352,348

DATED        : October 4, 1994

INVENTOR(S)  : Chung Chang Young et al.

It is certified that error appears in the above-identified patent and that said Letters Patent is hereby corrected as shown below:

```
Col. 1, line 16 "To" should be --to--.
Col. 3, line 26, "Thicker" should be --thicker--.
Col. 4, line 18, "This" should be --this--.
Col. 6, line 21, "factate" should be --lactate--.
Col. 6, line 53, "Substrate" should be --substance--.
Col. 6, line 59, "300" should be --500--.
Col. 7, lines 12 and 14, "Substrate" should be
        --substance--.
```

Signed and Sealed this

First Day of April, 1997

BRUCE LEHMAN

*Attesting Officer*     Commissioner of Patents and Trademarks